US012558439B2

(12) United States Patent (10) Patent No.: US 12,558,439 B2
Welzig et al. (45) Date of Patent: Feb. 24, 2026

(54) PROCESS FOR PRODUCING A CONTRAST AGENT

(71) Applicant: SANOCHEMIA PHARMAZEUTIKA GMBH, Neufeld an der Leitha (AT)

(72) Inventors: Stefan Welzig, Vienna (AT); Beate Kälz, Steinbrunn (AT); József Gungl, Ágfalva (HU); Klaus Gerdes, Kaarst Vorst (DE); Roswitha Braunrath, Eisenstadt (AT); Christina Abrahamsberg, Vienna (AT)

(73) Assignee: SANOCHEMIA PHARMAZEUTIKA GMBH, Neufeld an der Leitha (AT)

( * ) Notice: Subject to any disclaimer, the term of this patent is extended or adjusted under 35 U.S.C. 154(b) by 0 days.

(21) Appl. No.: 16/971,734

(22) PCT Filed: Feb. 20, 2019

(86) PCT No.: PCT/EP2019/054190
§ 371 (c)(1),
(2) Date: Aug. 21, 2020

(87) PCT Pub. No.: WO2019/162313
PCT Pub. Date: Aug. 29, 2019

(65) Prior Publication Data
US 2020/0390910 A1 Dec. 17, 2020

(30) Foreign Application Priority Data

Feb. 23, 2018 (AT) ............................... A 50162/2018

(51) Int. Cl.
*A61K 49/10* (2006.01)
(52) U.S. Cl.
CPC .................................. *A61K 49/108* (2013.01)
(58) Field of Classification Search
CPC ........................... C07D 257/02; A61K 49/108
See application file for complete search history.

(56) References Cited

U.S. PATENT DOCUMENTS

| | | | |
|---|---|---|---|
| 5,876,695 A | 3/1999 | Gries et al. | |
| 6,083,479 A | 7/2000 | Platzek et al. | |
| 2017/0266304 A1 * | 9/2017 | Thaning .............. | A61K 47/547 |

FOREIGN PATENT DOCUMENTS

| | | | |
|---|---|---|---|
| CN | 101977633 A | 2/2011 | |
| CN | 105073144 A | 11/2015 | |
| CN | 105209439 A | 12/2015 | |
| CN | 106999614 A | 8/2017 | |
| CN | 106999615 A | 8/2017 | |
| DE | 10 2015 013 939 | 3/2017 | |
| EP | 2242515 A2 * | 10/2010 | ............. A61K 31/28 |
| EP | 3159014 A1 * | 4/2017 | ............. A61K 31/28 |
| KR | 10-1466602 | 12/2014 | |
| WO | 03/011115 | 2/2003 | |
| WO | 2007/042504 | 4/2007 | |
| WO | 2009/103744 | 8/2009 | |
| WO | 2014/114664 | 7/2014 | |
| WO | 2014/160039 | 10/2014 | |
| WO | 2016/015066 | 2/2016 | |
| WO | 2016/083597 | 6/2016 | |
| WO | 2016/083600 | 6/2016 | |
| WO | 2017/046694 | 3/2017 | |

OTHER PUBLICATIONS

International Search Report for PCT/EP2019/054190 mailed May 31, 2019, 4 pages.
Austrian Search Report for A 50162/2018 mailed Dec. 28, 2018, 3 pages.
Communication according to Rule 114 (2) EPC issued by the European Patent Office on Jan. 19, 2021 regarding corresponding European Patent Application No. 19706593.1 along with Third-party observations.

* cited by examiner

*Primary Examiner* — Jennifer Chin
(74) *Attorney, Agent, or Firm* — NIXON & VANDERHYE

(57) ABSTRACT

Disclosed is a process for producing a contrast agent-containing pharmaceutical preparation, which contains as the contrast agent a complex of a lanthanide, in particular gadolinium, and a macrocyclic chelate, in particular DOTA.

15 Claims, 1 Drawing Sheet

| Material | Method step | In-process check |
|---|---|---|
| Water for the injection → | Sample water for the injection and set the temperature | Endotoxin check <br> Total bacterial count |
| DOTA → | Add DOTA (97%) | Appearance of the solution |
| Gd₂O₃ → | Add Gd₂O₃ (100%) <br> (Stir the solution at 80°C) | Appearance of the solution |
| Meglumine → | Add meglumine (99.8%) | Appearance of the solution <br> pH (usually above 7.2) |
| DOTA → | Add DOTA until the pH is below 5.0%. <br><br> The pH should preferably be between 4.6 and 4.7. | If necessary, additional test: A sample is checked using indicator solution for the meglumine ratio: the colour of the solution should show whether the reaction is complete. |
| DOTA → | If necessary, add DOTA up to 500 - 700 ppm. <br> Preferably 700 ppm | pH 4.2 - 4.5 |
| Meglumine → | Adjust pH using meglumine | pH 7.0 - 7.5 |
| Water for the injection → | Adjust the final volume | Total bacteria count |

PROCESS FOR PRODUCING A CONTRAST AGENT

This application is the U.S. national phase of the International Application No. PCT/EP2019/054190 filed Feb. 20, 2019 which designated to the U.S. and claims priority to Austrian Patent Application No. A 50162/2018 filed Feb. 23, 2018, the entire contents of each of which are hereby incorporated by reference.

Background of the invention

Field of the Invention

The invention relates to a method for producing a preparation containing a complex of a macrocyclic chelate, such as DOTA (1,4,7,10-tetraazacyclododecane-1,4,7,10-tetraacetic acid), with a lanthanide, such as gadolinium, and additionally a base, such as L-lysine or meglumine.

Description of the Related Art

The preparation producible in accordance with the invention can be used as a contrast agent, in particular for magnetic resonance ("MR"). Such preparations are known.

For example, a preparation marketed by GUERBET (France) under the brand name "DOTAREM" is known. DOTAREM contains a complex gadolinium and DOTA ("gadoteric acid") as MR contrast agent as well as free DOTA.

Also known are various methods for producing preparations containing a complex of a lanthanide, in particular gadolinium, a macrocyclic chelate, such as DOTA (=1,4,7,10-tetraazacylododecane-N,N',N'',N'''-tetraacetic acid), free DOTA and a base, such as meglumine.

For example, reference is made to WO 2009/103744 A2 and WO 2016/015066 A1.

The preparation obtainable according to WO 2009/103744 A2 contains DOTA as a free macrocyclic chelate in a mol/mol amount between 0.002 and 0.4%.

The methods known from WO 2009/103744 A2 and from WO 2016/015066 A1 use lanthanide, such as gadolinium, and macrocyclic chelate, such as DOTA, not in equimolar amounts, but either with an excess of lanthanide or with an excess of macrocyclic chelate. In WO 2009/103744 A2 a method in which the lanthanide and the macrocyclic chelate are used in equimolar (=stoichiometric) amounts is noted as not being industrially applicable (WO 2009/103744 A2, page 5).

DE 10 2015 013 939 A1 and WO 2017/046694 A1 disclose a method for producing a liquid pharmaceutical formulation of gadoteric acid meglumine comprising the steps:
  a) mixing a predetermined amount of gadolinium oxide, DOTA and meglumine in water;
  b) adjusting the pH of the mixture to a pH between 6.5 and 8.0 by adding DOTA or an acid, wherein the amount of free DOTA is in the range of 0.002 to 0.5% and the content of free gadolinium is less than 0.02%.

However, the method known from WO 2017/046694 A1 does not exclude the presence of up to 200 ppm free gadolinium in the formulation.

Brief summary of the invention

The object of the invention is that of providing a simple and industrially practicable method for producing the preparation usable as a contrast agent.

This object is achieved by a method that comprises the steps mentioned in the independent claim.

Preferred and advantageous embodiments of the method according to the invention are the subject of the dependent claims.

The macrocyclic chelate which is usable within the scope of the present invention is advantageously selected from the following chelates: DOTA, NOTA, DO3A, BT-DO3A, HPDO3A, POTA, DOTAGA and derivatives thereof, and is particularly preferably DOTA. The chemical formulae of these chelates are known and are given, for example, in WO 2007/042 504 on pages 20 to 23 and in WO 2003/011 115 on pages 8 to 11.

Within the scope of the invention, all lanthanides are considered, in particular gadolinium, europium and dysprosium, and preferably gadolinium.

Due to its content of free macrocyclic chelate, such as DOTA, the preparation obtainable in accordance with the invention has the advantage that it is ensured, in any case, that the preparation does not contain free lanthanide, i.e. not complexed with macrocyclic chelate, such as gadolinium, or at most contains it in an amount of less than 20 ppm.

The method according to the invention has the advantage that it can be carried out without great effort, with good yields and without detrimental by-products.

In particular, the method according to the invention, in one possible embodiment, allows it to be carried out with equimolar amounts of lanthanide, such as gadolinium, and of macrocyclic chelate, such as DOTA, i.e. in the production of gadoteric acid, with good yields and on an industrial scale.

The lanthanide can advantageously be added in oxide form (in particular as gadolinium oxide), but the invention also considers other possible forms of lanthanide, especially lanthanide salts.

Surprisingly, when carrying out the method according to the invention in the embodiment with stoichiometric (equimolar) as well as with non-stoichiometric amounts of lanthanide, especially gadolinium, and macrocyclic chelate, such as DOTA, in the reaction mixture, the complexing (forming of the complex from the lanthanide, such as gadolinium, and macrocyclic chelate, such as DOT) is completed in one step.

This also applies if the amounts of macrocyclic chelate and lanthanide in the reaction mixture are selected in such a way that not all of the lanthanide is initially complexed by the macrocyclic chelate.

Furthermore, when carrying out the method according to the invention with stoichiometric (equimolar) or non-stoichiometric quantities of lanthanide, in particular gadolinium, and macrocyclic chelate, such as DOTA, in the reaction mixture, it is advantageous that the complexing (forming of the complex from the lanthanide, such as gadolinium, and macrocyclic chelate, such as DOTA) is well started at a pH in the acidic range (pH<4.5), for example at a pH between 2.0 and 4.0. The complexing then proceeds rapidly and completely in the presence of the base, such as meglumine, at a pH in a less acidic range, for example at a pH of from 4.0 to 8.0.

BRIEF DESCRIPTION OF THE DRAWING

The single FIGURE is a flowchart that schematically illustrates an embodiment of the process for producing a contrast agent. The flowchart outlines the sequential addition of materials, the specific method steps performed, and the corresponding in-process checks carried out during the manufacturing process.

DETAILED DESCRIPTION OF THE INVENTION

The method according to the invention can be carried out in various embodiments.

The percentages used in the examples and hereinafter relate to the stoichiometric amount leading to 100% in the content of the complex of lanthanide and macrocyclic chelate in the finished final product. Thus, 100% means the theoretical weight that leads to 100% content of complex in the finished product.

For example, "98% DOTA" means that DOTA is present in a molar amount of substance of 98% relative to the molar amount of substance of gadolinium (oxide) used. Accordingly, "99.8% meglumine" means that meglumine is present in a molar amount of substance of 99.8% relative to the molar amount of substance of gadolinium (oxide) used.

In a preferred embodiment of the method according to the invention, the production of the pharmaceutical preparation, in particular the step of complexing lanthanide with a macrocyclic chelate with regulation of the pH values during the course of the production method is particularly favourable if the ratio of the starting materials used is correctly selected.

It has been found that a deficit of lanthanide (for example in the form of gadolinium oxide) impedes the production with regulation of the pH values and an excessive deficit of lanthanide makes successful production almost impossible.

In a preferred embodiment, the method according to the invention, specifically the production of the complex of lanthanide and macrocyclic chelate, in particular the gadolinium-DOTA complex (gadoteric acid), has the advantage that it can be carried out with good yields via the pH regulation, even in the case of different proportions (substoichiometric to overstoichiometric ratios) of the starting materials.

An industrially successfully applicable and thus effective production of the preparation (for example of the gadolinium-DOTA complex with the method according to the invention) which can be carried out in practice with good results can lead to well reproducible results with the exemplary proportions mentioned below:

gadolinium oxide: 100%

DOTA: 95 to 100%, a range of 97 to 98% being preferred meglumine: 99.5 to 100%, a range of 99.7 to 99.8% being preferred.

In the case of a starting amount of 100% lanthanide (for example in the form of gadolinium oxide), it has been found to be advantageous in the method according to the invention if the ratio of DOTA to meglumine is 98 to 99.8%.

Surprisingly, when carrying out the method according to the invention, it has been shown that an embodiment in which the production is controlled by regulating the pH in the reaction mixture is advantageous if the amount of meglumine is chosen such that meglumine is sub-stoichiometric with respect to the lanthanide (for example in the form of gadolinium oxide) but has a stoichiometric excess of about 2% with respect to the macrocyclic chelate (such as DOTA).

An example of the production of a liquid preparation according to the invention containing a complex of a lanthanide (for example gadolinium) and a macrocyclic chelate (for example DOTA) as MR contrast agent is described below:

To produce a liquid pharmaceutical preparation containing the complex of the macrocyclic chelate with a lanthanide and free macrocyclic chelate, a solution containing the chelate and the lanthanide is stirred so as to complex the lanthanide by the macrocyclic chelate. The amount of chelate and the amount of lanthanide are chosen so that not all of the lanthanide is complexed (overstoichiometric amount of lanthanide). Meglumine is added to the solution in order to adjust the pH.

By adding DOTA, the pH of the mixture is adjusted to a pH below 5.5.

In a further step, the pH of the solution is adjusted to between 6.8 and 7.5 using a base, preferably meglumine.

In the finished preparation, the mol/mol amount of free chelate (for example DOTA) is in the range of from 0.001 to 0.5%.

With an (optimal) 1:1 ratio of gadolinium and meglumine in the solution, the desired proportion of free DOTA is present when the pH of 5.0 to 5.5 is reached by the H-controlled addition of DOTA. The ratio can also be checked, in a supportive manner, by an indicator reaction. Thus, at the end of the production of the preparation, a rapid test can be used if necessary (preferably). This can be an indicator reaction.

The indicator reaction can be carried out as follows, with the statement of the indicator reaction being of significance only below a pH of the solution of 5.55:

80 µl of a xylenol gel indicator solution and 40 ml of water are added to 0.1 ml of sample from the reaction mixture. If the solution is pink, this indicates that an equilibrium has not yet been reached in the reaction. The meglumine proportion lowers the pH in the reaction mixture to a lower pH in order to achieve the desired proportion of free DOTA.

Advantages of the method according to the invention are:

very simple, large-scale industrial process;

easy and fast process management;

the production is based on a specific adjustment of the pH without complex in-process checks;

the production can be performed in a single vessel;

the technical challenges, such as water content of the starting materials or the problem of the presence of possible free gadolinium in the range above 20 ppm, are bridged, thus ensuring a higher product safety.

The steps of the example shown in the drawing for the production of a total solution containing gadoteric acid on an industrial scale are explained in more detail below:

The production of the total solution is carried out in a class C clean room.

Before starting the production of the total solution, the necessary equipment and other parts of the filling are autoclaved, preferably for at least 30 minutes at more than 121° C. To produce the total solution, the defined amount of water for injection is introduced into a reaction vessel and a temperature above 70° C., preferably between 70° C. and 80° C., is Step 1:

Provide water for injection and set the temperature of the water for injection to between 70° C. and 80° C.

Step 2:

Add DOTA, 97%, relative to the anhydrous substance

Step 3:

Add gadolinium oxide, 100%, relative to the pure substance Stir the reaction mixture (solution).

Step 4:

Add meglumine, 99.8%, relative to the theoretical amount used.

Step 5:

Add DOTA until the pH of the solution is less than 5.5. In particular, the pH should be between 4.5 and 5.0, preferably between 4.6 and 4.8.

Step 6:

If necessary (optionally), add DOTA in an amount of from 500 to 700 ppm, preferably 700 ppm, calculated on the final concentration of the complex in the finished pharmaceutical preparation.

Step 7:

Adjust the pH using meglumine to a value between 7.0 and 7

Step 8:

Adjust the final volume with water for injection.

The final total solution is filtered, in particular the solution can be filtered sterile, and is then filled into bottles with an appropriate filling volume.

Immediately after filling, the bottles are sealed and finally sterilised in an autoclave.

Description of the Preferred Embodiments

Examples of the method according to the invention are given below:

Example 1: Amounts: DOTA: 97.0%, Meglumine: 99.8%

104.22 g DOTA (the weight is corrected according to the water content and calculated to 97.0%) are dissolved in approx. 300 ml water at a temperature of from 75° C. to 80° C. 45.59 g of gadolinium oxide (the weight was corrected according to the purity) are added and the mixture is stirred at a temperature of at least 75° C. for at least one hour. 43.71 g meglumine are then added to the solution, which is then stirred at a temperature of least at 75° C. for at least one hour. The pH of the solution is approx. 7. By adding a defined amount of DOTA, the pH of the solution is adjusted to approx. 6 (for example pH=6.3). DOTA is added to the solution in small portions with the aim of adjusting the pH to below 5.5, preferably to below 5.0. After the pH of 4.9 is reached, DOTA corresponding to 660 ppm is also added to the solution. The pH of 4.4 is then adjusted to using meglumine. The reaction mixture is made up to a total volume of 500 ml, filtered and autoclaved.

Example 2: Amounts: DOTA: 98.0%, Meglumine: 99.7%

106.20 g DOTA (the weight is corrected according to the water content and calculated to 98.0%) are dissolved in approx. 300 ml water at a temperature of from 75° C. to 30° C. 45.59 g of gadolinium oxide (the weight was corrected according to the purity) are added and the mixture is stirred at a temperature of at least 75° C. for at least one hour. 48.66 g meglumine are then added to the solution, which is then stirred at a temperature of least at 75° C. for at least one hour. The pH of the solution is approx. 7. By adding a defined amount of DOTA, the pH of the solution is adjusted to approx. 6 (pH=6.1). DOTA is added to the solution in small portions with the aim of adjusting the pH to below 5.5, preferably to below 5.0. After the pH of 4.4 is reached, DOTA corresponding to 620 ppm is also added to the solution. The pH of 3.9 is then adjusted to 7.1 using meglumine.

The reaction mixture is made up to a total volume of 500 ml, filtered and autoclaved.

Example 3: Amounts: DOTA: 98.0%, Meglumine: 99.5%

106.20 g DOTA (the weight is corrected according to the water content and calculated to 98.0%) are dissolved in approx. 300 ml water at a temperature of from 75° C. to 80° C. 45.59 g of gadolinium oxide (the weight was corrected according to the purity) are added and the mixture is stirred at a temperature of at least 75° C. for at least one hour. 48.56 g meglumine are then added to the solution, which is then stirred at a temperature of least at 75° C. for at least one hour. The pH of the solution is approx. 7. By adding a defined amount of DOTA, the pH of the solution is adjusted to approx. 6 (pH=5.9). DOTA is added to the solution in small portions with the aim of adjusting the pH to below 5.5, preferably to below 5.0. After the pH of 4.7 is reached, DOTA corresponding to 910 ppm is also added to the solution. The pH of 4.1 is then adjusted to 7.1 using meglumine. The reaction mixture is made up to a total volume of 500 ml, filtered and autoclaved.

| Example number | Mixture number | Free DOTA amount in the autoclaved final product (ppm) |
|---|---|---|
| Example 1 | E-17-0087-G | 934 |
| Example 2 | E-17-0086-G | 797 |
| Example 3 | E-17-0077-G | 460 |

The above-mentioned indicator reaction to determine the ratio of DOTA and meglumine and to check the equilibrium in the solution can be carried out in all cases in a supportive manner, so that fluctuations in the starting proportions of the three starting materials—mixed in a preparation vessel—can be well tracked.

As shown in the examples, the final content of excess DOTA can be adjusted to approx. 200 to 2000 ppm in the method according to the invention.

In the case of industrial amounts, the filling to the total volume is a step in which, with well-defined starting amounts, the adjustment to the final volume often requires only a small change, thus eliminating the need to readjust the amount of free DOTA.

If necessary, a corresponding adjustment can be made on a laboratory scale before the autoclaving.

In summary, an embodiment of the invention can be described as follows:

A method for producing a contrast-agent-containing pharmaceutical preparation, which contains, as contrast agent, a complex of a lanthanide, in particular gadolinium, and a macrocyclic chelate, in particular DOTA, is described.

The invention claimed is:

1. A method for producing an aqueous liquid preparation containing, as contrast agent for magnetic resonance, a complex of a lanthanide and a macrocyclic chelate, the preparation containing free macrocyclic chelate, the method comprising:

a) dissolving a macrocyclic chelate in water, b) adding a lanthanide, c) adding meglumine, d) carrying out the complexing of the lanthanide with the macrocyclic chelate, in the presence of the meglumine, at a pH between 6.5 and 8.0, wherein the lanthanide is present in molar excess to meglumine and wherein meglumine is present in molar excess to the macrocyclic chelate, e) adjusting the pH of the solution obtained after step d) to a target pH value below 5.0 by stepwise adding an acid in increments, e1) after the target pH value has been reached, adding a final amount of the acid, f) after step e1), adjusting the pH to a value above 6.5, and g) diluting the solution obtained after step f) to the specified final volume, wherein the method is performed in a single vessel; and wherein the method is further defined as an industrial-scale method.

2. The method according to claim 1, wherein gadolinium is used as the lanthanide.

3. The method according to claim 2, wherein the lanthanide is gadolinium oxide.

4. The method according to claim 2, wherein DOTA is used as the macrocyclic chelate.

5. The method according to claim 1, wherein the lanthanide is gadolinium oxide.

6. The method according to claim 5, wherein DOTA is used as the macrocyclic chelate.

7. The method according to claim 1, wherein DOTA is used as the macrocyclic chelate.

8. The method according to claim 1, wherein said acid is DOTA.

9. The method according to claim 8, wherein said final amount is 500 to 799 ppm.

10. The method according to claim 1, wherein the pH in step f) is adjusted to a value between 6.5 and 8.0.

11. The method according to claim 1, wherein the adjustment of the pH in step f) is carried out with meglumine.

12. The method of claim 1, wherein step f) is performed to adjust the pH to a value above 7.0.

13. The method of claim 1, wherein step f) is performed to adjust the pH to a value between 7.0 and 7.5.

14. A method for producing an aqueous liquid preparation containing, as contrast agent for magnetic resonance, a complex of gadolinium and DOTA, the preparation containing free DOTA, the method comprising:

a) dissolving DOTA in water, b) adding gadolinium, c) adding meglumine, d) carrying out the complexing of gadolinium with DOTA, in the presence of the meglumine, at a pH between 6.5 and 8.0, wherein gadolinium is present in molar excess to meglumine and wherein meglumine is present in molar excess to DOTA, e) adjusting the pH of the solution obtained after step d) to a target pH value below 5.0 by stepwise adding further DOTA in increments, e1) after the target pH value has been reached, adding a final amount of DOTA, f) after step e1), adjusting the pH to a value above 6.5, and g) diluting the solution obtained after step f) to the specified final volume, wherein the method is performed in a single vessel; and wherein the method is further defined as an industrial-scale method.

15. A method for producing an aqueous liquid preparation containing, as contrast agent for magnetic resonance, a complex of gadolinium and DOTA, the preparation containing free DOTA, the method comprising:

a) dissolving DOTA in water, b) adding gadolinium, c) adding meglumine, d) carrying out the complexing of gadolinium with DOTA, in the presence of the meglumine, at a pH between 6.5 and 8.0, wherein gadolinium is present in molar excess to meglumine and wherein meglumine is present in molar excess to DOTA, e) adjusting the pH of the solution obtained after step d) to a target pH value below 5.0 by stepwise adding further DOTA in increments, e1) after the target pH value has been reached, adding a final amount of DOTA, f) after step e1), adjusting the pH to a value above 6.5 by adding further meglumine, and g) diluting the solution obtained after step f) to the specified final volume, wherein the solution contains free DOTA, wherein the free DOTA in the solution is up to 2000 ppm;

wherein the method is performed in a single vessel; wherein at least both of the following in-process checks are performed when performing the method: endotoxin check and total bacterial count, and wherein the method is further defined as an industrial-scale method.

* * * * *